US00PP12118P2

(12) United States Plant Patent
Zary

(10) Patent No.: US PP12,118 P2
(45) Date of Patent: Oct. 2, 2001

(54) HYBRID TEA ROSE PLANT NAMED 'JACOLFA'

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 09/455,228

(22) Filed: Dec. 6, 1999

(51) Int. Cl.[7] ..... A01H 5/00
(52) U.S. Cl. ..... Plt./137
(58) Field of Search ..... Plt./137, 133, 130

*Primary Examiner*—Howard J. Locker
(74) *Attorney, Agent, or Firm*—Klarquist Sparkman Campbell Leigh & Whinston, LLP

(57) ABSTRACT

A hybrid tea rose plant having vigorous, upright growth; large, soft pink flowers of old fashioned form and strong, sweet fragrance; dark green, glossy foliage and resistance to rust and mildew.

1 Drawing Sheet

The present invention relates to a new and distinct variety of rose plant of the hybrid tea class which was originated by me by crossing the variety JACale (U.S. Plant Pat. No. 5,860), with the variety Silver Jubilee (not patented).

The primary objective of this breeding was to produce a new rose variety having the large flower size, soft color and strong fragrance of the female parent, combined with the vigorous, upright growth, glossy, dark green foliage and resistance to disease of the male parent. The objective was substantially achieved, along with other desirable improvements, as evidenced by the following unique combination of characteristics that are outstanding in the new variety and that distinguish it from its parents, as well as from all other varieties of which I am aware:

1. Strong fragrance;
2. Old fashioned flower form;
3. Dark green, glossy foliage;
4. Soft pink flower color;
5. Vigorous, upright growth; and
6. Resistance to mildew and rust.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:
*Seed parent.*—JACale (U.S. Plant Pat. No. 5,860).
*Pollen parent.*—Silver Jubilee (not patented).

Classification:
*Botanical.*—*Rosa hybrida.*
*Commercial.*—Hybrid tea.

FLOWER

Observations made from specimens grown in a garden environment at Somis, Calif. from March 1998 to August 1999.

Blooming habit: Continuous.

Bud:
*Size.*—About 1½ inches long when the petals start to unfurl.
*Form.*—The bud form is short; globular.
*Color.*—When sepals first divide, bud color is Green-Yellow Group 1C with areas of red group 48D. When half blown, the upper and lower sides of the petals are Red Group 36D.
*Sepals.*—Color: Green Group 138B. Surface texture: Covered in fine hairs. There are three lightly appendaged sepals. There are two unappendaged sepals with hairy edges.
*Receptacle.*—Color: Green Group 137B. Shape: Funnel. Size: Medium (about 7/16 inch×3/8 inch). Surface: Smooth.
*Peduncle.*—Length: Medium (about 3 to 3½ inches). Surface: Smooth. Color: Green Group 137B. Strength: Stiff, erect.

Bloom:
*Size.*—Large. Average open size is about 4 to 4½ inches.
*Borne.*—Singly.
*Stems.*—Strength: Strong. Average length is about 18 to 22 inches.
*Form.*—When first open: Globular. Permanence: Retains its form to the end.
*Petalage.*—Number of petals under normal conditions: 40 to 50.
*Color.*—The upper and reverse sides of the petals are Red group 36D. The base of each petal has a small, 3/16 inch×3/16 inch, Yellow Group 2D half moon on both surfaces at the point of attachment. The major color on the upper side is Red Group 36D.
*Variegations.*—Occassional greenish streaks on the guard petals.
*Discoloration.*—The general tonality at the end of the first day: No change. At the end of the third day: No change.
*Fragrance.*—Strong; sweet.

Petals:
*Texture.*—Thick.
*Shape.*—Round.

*Form.*—Tips slightly recurved.

*Arrangement.*—Imbricated; no petaloids in the center.

*Persistence.*—Petals drop off cleanly before drying.

*Lastingness.*—On the plant: Fair (about five or six days). As a cut flower: Fair (about six or seven days).

*Other traits or characteristics.*—The globular bud opens to a flower filled with petals. The open flower sometimes has a quartered but always crowded look, giving the bloom an old fashioned look.

Reproductive parts:

*Anthers.*—Size: Medium. Quantity: Many. Color: Orange Group 24D. Arrangement: Regular around styles.

*Filaments.*—Color: Yellow-Orange Group 23D.

*Pollen.*—Present.

*Styles.*—Color: Red Group 53B.

*Stigmas.*—Color: Orange-White Group 159C.

Plant:

*Form.*—Bush.

*Growth.*—Vigorous; upright; branching. At maturity, height is five feet, width is 3½ feet.

Foliage: Number of leaflets on normal mid-stem leaves: five or seven.

*Size.*—Large (six inches long×four inches wide).

*Quantity.*—Abundant.

*Color.*—New foliage: Upper and lower surfaces: Greyed-Red Group 178A. Old foliage: Upper surface: Green Group 139A. Lower surface: Green Group 137D.

Leaflets:

*Shape.*—Pointed oval.

*Texture.*—Leathery; glossy.

*Edge.*—Smooth; serrated.

*Serration.*—Single; small.

*Petiole rachis.*—Color: Green Group 137B on the upper surface, Green Group 137D on the lower surface.

*Petiole underside.*—Smooth; with occasional prickles.

*Stipules.*—Short (about ⅜ inch); bearded.

*Disease resistance.*—Resistant to mildew and rust, susceptible to blackspot under normal growing conditions.

Wood:

*New wood.*—Color: Greyed-Red Group 178A turning green very quickly. Bark: Smooth.

*Old wood.*—Color: Green Group 137B. Bark: Smooth.

Prickles:

*Quantity.*—On main canes from base: Ordinary. On laterals from main canes: Ordinary.

*Form.*—Medium; hooked downward.

*Color when young.*—Greyed-Red Group 178C.

*Color when mature.*—Greyed-Orange Group 177A.

Small prickles:

*Quantity.*—On main stalks: None. On laterals: None.

I claim:

1. A new and distinct variety of rose plant of the hybrid tea class, substantially as herein shown and described, characterized particularly by its vigorous, upright growth; large, soft pink flowers of old fashioned form and strong, sweet fragrance; dark green, glossy foliage and resistance to rust and mildew.

* * * * *

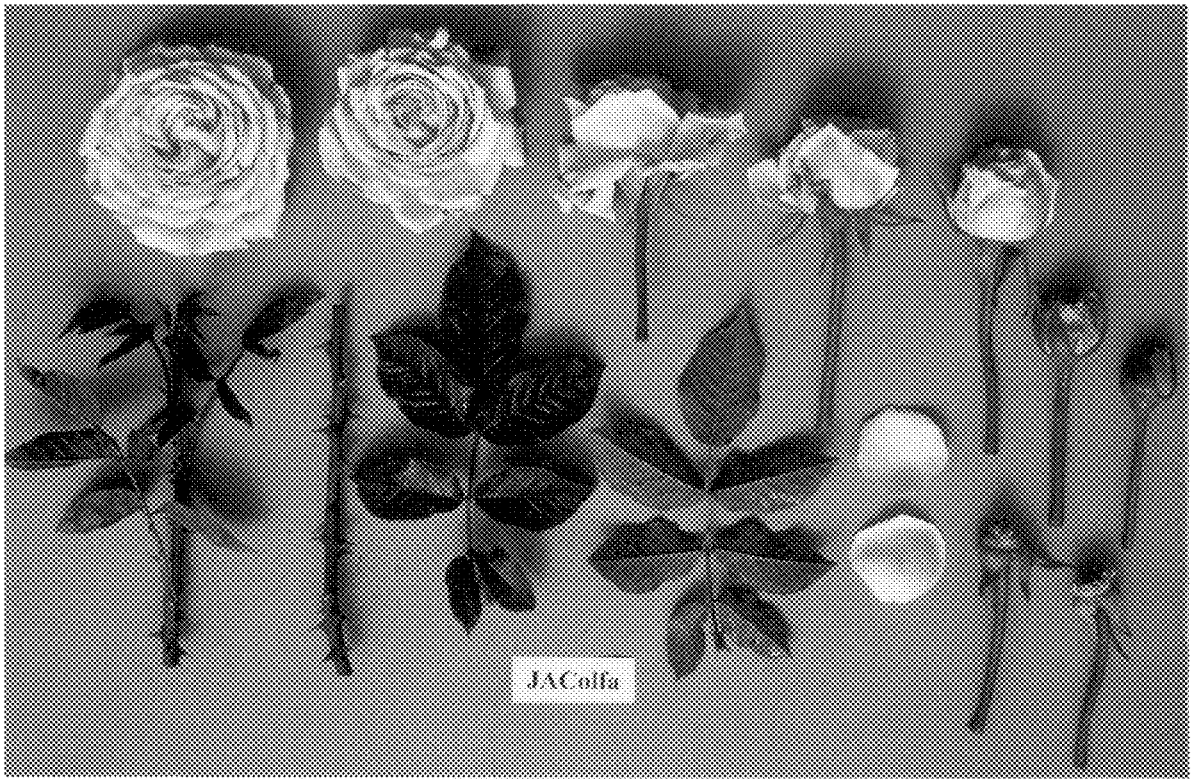
JACoffa